US007205111B2

(12) United States Patent
Christensen et al.

(10) Patent No.: US 7,205,111 B2
(45) Date of Patent: Apr. 17, 2007

(54) RAPID IDENTIFICATION OF BACTERIA FROM POSITIVE BLOOD CULTURES

(75) Inventors: Jeffrey E. Christensen, Pullman, WA (US); Pamela J. Squires, Marshfield, WI (US); Kurt D. Reed, Marshfield, WI (US)

(73) Assignee: Marshfield Clinic, Marshfield, WI (US)

( * ) Notice: Subject to any disclaimer, the term of this patent is extended or adjusted under 35 U.S.C. 154(b) by 0 days.

(21) Appl. No.: 10/897,592

(22) Filed: Jul. 23, 2004

(65) Prior Publication Data
US 2005/0037408 A1    Feb. 17, 2005

Related U.S. Application Data

(60) Provisional application No. 60/489,947, filed on Jul. 24, 2003.

(51) Int. Cl.
*C12Q 1/68* (2006.01)
*C12P 19/34* (2006.01)
*G06F 19/00* (2006.01)

(52) U.S. Cl. .................. 435/6; 435/91.2; 700/104.1
(58) Field of Classification Search .................... 435/6, 435/91.2
See application file for complete search history.

(56) References Cited

U.S. PATENT DOCUMENTS 6,177,266 B1    1/2001 Krishnamurthy et al.
6,613,520 B2    9/2003 Ashby

FOREIGN PATENT DOCUMENTS

WO        WO 9513396 A2 *    5/1995

OTHER PUBLICATIONS

Turenne et al. (Rapid Identification of Bacteria from Positive Blood Cultures by Fluorescence-Based PCR-Single-Strand Conformation Polymorphism Analysis of the 16S rRNA Gene Journal of Clinical Microbiology. Feb. 2000. vol. 38, No. 2: pp. 513-520).*
Nowak et al. "Differentiation of seventeen genospecies of Acinetobacter by multiplex polymerase chain reaction and restriction fragment length polymorphism analysis" Molecular and Cellular Probes. 1996. No. 10: pp. 405-411).*
Marsh et al. "Terminal Restriction Fragment Length Polymorphism Analysis Program, A Web-Based Research Tool for Microbial Community Analysis" Applied and Environmental Microbiology. Aug. 2000. vol. 36, No. 8: pp. 3616-3620).*
Liu et al. (Characterization of Microbial Diversity by Determining Terminal Resriction Fragment Length Polymorphisms of Genes Encoding 16S rRNA Applied and Environmental Microbiology. Aug. 1997. vol. 63, No. 11: pp. 4516-4522).*
Liu et al. ("Characterization of microbial diversity by determining terminal restriction fragment length polymorphisms of genes encoding 16S rRNA" Appl Environ Microbiol. Nov. 1997;63(11):4516-22).*

Bernhard et al. ("Identification of nonpoint sources of fecal pollution in coastal waters by using host-specific 16S ribosomal DNA genetic markers from fecal anaerobes" Appl Environ Microbiol. Apr. 2000;66(4):1587-94).*
Marsh et al. "Terminal Restriction Fragment Length Polymorphism Analysis Program, A Web-Based Research Tool for Microbial Community Analysis" Applied and Environmental Microbiology. Aug. 2000. vol. 36, No. 8: pp. 3616-3620).*
Turenne et al. (Rapid Identification of Bacteria from Positive Blood Cultures by Fluorescence-Based PCR-Single-Strand Conformation Polymorphism Analysis of the 16S rRNA Gene Journal of Clinical Microbiology. Feb. 2000. vol. 38, No. 2: pp. 513-520).*
Amann, R. I., W. Ludwig, and K. H. Schleifer. 1995. Phylogenetic identification and in situ detection of individual microbial cells without cultivation. Microbio. Rev. 59:143-169.
Avaniss-Aghajani, E., K. Jones, A. Holtzman, T. Aronson, N. Glover, M. Boian, S. Froman, C. F. Brunk. 1996. Molecular technique for rapid identification of Mycobacteria. J. Clin. Microbiol. 34:98-102.
Brakstad, O. G., K. Aasbakk, and J. A. Maeland. 1992. Detection of *Staphylococcus aureus* by polymerase chain reaction amplification of the *nuc* gene. J. Clin. Microbiol. 30:1654-1660.
Browne, K., J. Miegel, and K. D. Stottmeier. 1984. Detection of pneumococci in blood cultures by latex agglutination. J. Clin. Microbiol. 19:649-650.
Brunk, C. F., E. Avaniss-Aghajani, and C. A. Brunk. 1996. A computer analysis of primer and probe hybridization potential with bacterial small-subunit rRNA sequences. Appl. Environ. Microbiol. 62:872-879.
Chen, K., H. Neimark, P. Rumore, and C. R. Steinman. 1989. Broad range DNA probes for detecting and amplifying eubacterial nucleic acids. FEMS Microbiol. Lett. 48:19-24.
Chen, Y. C., J. D. Eisner, M. M. Kattar, S. L. Rassoulian-Barrett, K. Lafe, U. Bui, A. P. Limaye, and B. T. Cookson. 2001. Polymorphic internal transcribed spacer region 1 DNA sequences identify medically important yeasts. J. Clin. Microbiol. 39:4042-4051.
Denis, F., J. Fleurette, G. Laurans, A. Moulin, M. Mounier, J. Orfila, and M. E. Reverdy. 1984. A latex agglutination technique for rapid, direct identification of pneumococci in blood cultures. Eur. J. Clin. Microbiol. 3:321-322.

(Continued)

*Primary Examiner*—Young J. Kim
*Assistant Examiner*—Christopher M. Babic
(74) *Attorney, Agent, or Firm*—DeWitt Ross & Stevens S.C.; Charles S. Sara (57) ABSTRACT

Disclosed is a method of detecting bacteria in a biological sample, especially a blood sample, without the need for extensive sub-culturing of the sample. Nucleic acid present within the sample is isolated and bacterial DNA specifically amplified using primers that uniquely prime the amplification of 16s rRNA-encoding nucleic acid. The amplicons are then digested with an endonuclease to yield a restriction fragment length profile for the biological sample. The restriction fragment length profile for the biological sample is then compare to a database of profiles made using cultures of known bacterial species. A match between the sample profile and the database identifies the bacteria present in the sample.

14 Claims, 4 Drawing Sheets

OTHER PUBLICATIONS

Doern, G. V., R. Vautour, M. Gaudet, and B. Levy, 1994. Clinical impact of rapid in vitro susceptibility testing and bacterial identification. J. Clin. Microbiol. 32:1757-1762.

Fredricks, D. N., and D. A. Relman, 1998. Improved amplification of microbial DNA from blood cultures by removal of the PCR inhibitor sodium polyanetholesulfonate, J. Clin. Microbiol., 36:2810-2816.

Fredricks, D. N. and D. A. Relman. 1999. Application of polymerase chain reaction to the diagnosis of infectious diseases. Clin. Infect. Dis. 29:475-486.

Gordon, L. P., M. A. Damm, and J. D. Anderson. 1987. Rapid presumptive identification of streptococci directly from blood cultures by serologic tests and the L-pyrrolidonyl-beta-naphthylamide reaction. J. Clin. Microbiol. 25:238-241.

Grisold, A. J., E. Leitner, G. Muhlbauer, E. Marth, and H. H. Kessler. 2002. Detection of methicillin-resistant *Staphylococcus aureus* and simultaneous confirmation by automated nucleic acid extraction and real-time PCR. J. Clin. Microbiol. 40:2392-2397.

Jarvis, W. R. 1996. Selected aspects of the socioeconomic impact of nosocomial infections: morbidity, mortality, cost, and prevention. Infect. Control Hosp. Epidemiol. 17:552-557.

Kitts, C. L. 2001. Terminal restriction fragment patterns: a tool for comparing microbial communities and assessing community dynamics. Curr. Issues Intest. Microbiol. 2:17-25.

Lem, P., J. Spiegelman, B. Toye, and K. Ramotar. 2001. Direct detection of *mecA*, nuc and 16S rRNA genes in BacT/Alert blood culture bottles. Diagn. Microbiol. Infect. Dis. 41:165-168.

Louie, L., J. Goodfellow, P. Mathieu, A. Glatt, M. Louie, and A. E. Simor. 2002. Rapid detection of methicillin-resistant staphylococci from blood culture bottles by using a multiplex PCR assay. J. Clin. Microbiol. 40:2786-2790.

Maes, N., J. Magdalena, S. Rottiers, Y. De Gheldre, and M. J. Struelens. 2002. Evaluation of a triplex PCR assay to discriminate *Staphylococcus aureus* from coagulase-negative Staphylococci and determine methicillin resistance from blood cultures. J. Clin. Microbiol. 40:1514-1517.

Maidak, B. L., J. R. Cole, T. G. Lilburn, C. T. Parker Jr., P. R. Saxman, R. J. Farris, G. M. Garrity, G. J. Olsen, T. M. Schmidt and J. M. Tiedje. 2001. The RDP-II (Ribosomal Database Project). Nucleic Acids Research. 29:173-174.

Maquelin, K., C. Kirschner, L. P. Choo-Smith, N. A. Ngo-Thi, T. van Vreeswiijk, M. Stammler, H. P. Endtz, H. A. Bruining, D. Naumann, and G. J. Puppels. 2003. Prospective study of the performance of vibrational spectroscopies for rapid identification of bacterial and fungal pathogens recovered from blood cultures. J. Clin. Microbiol. 41:324-329.

Marsh, T. L. 1999. Terminal restriction fragment length polymorphism (T-RFLP): an emerging method for characterizing diversity among homologous populations of amplification products. Curr. Opin. Microbiol. 2:323-327.

Marsh, T. L., P. Saxman, J. Cole, and J. Tiedje. 2000. Terminal restriction fragment length polymorphism analysis program, a web-based research tool for microbial community analysis. Appl. Environ. Microbiol. 66:3616-3620.

Murakami, K., W. Minamide, K. Wada, E. Nakamura, H. Teraoka, and S. Watanabe. 1991. Identification of methicillin-resistant strains of staphylococci by polymerase chain reaction. J. Clin. Microbiol. 29:2240-2244.

Oliveira, K., S. M. Brecher, A. Durbin, D. S. Shapiro, D. R. Schwartz, P. C. De Girolami, J. Dakos, G. W. Procop, D. Wilson, C. S. Hanna, G. Haase, H. Peltroche-Llacsahuanga, K. C. Chapin, M. C. Musgnug, M. H. Levi, C. Shoemaker, and H. Stender. 2003. Direct identification of *Staphylococcus aureus* from positive blood culture bottles. J. Clin. Microbiol. 41:889-891.

Qian, Q., Y. W. Tang, C. P. Kolbert, C. A. Torgerson, J. G. Hughes, E. A. Vetter, W. S. Harmsen, S. O. Montgomery, F. R. Cockerill, 3rd, and D. H. Persing. 2001. Direct identification of bacteria from positive blood cultures by amplification and sequencing of the 16S rRNA gene: evaluation of BACTEC 9240 instrument true-positive and false-positive results. J. Clin. Microbiol. 39:3578-3582.

Ratner, H. B., and C. W. Stratton. 1985. Thermonuclease test for same-day identification of *Staphylococcus aureus* in blood cultures. J. Clin. Microbiol. 21:995-996.

Relman, D. A., J. S. Loutit, T. M. Schmidt, S. Falkow, and L. S. Tompkins. 1990. The agent of bacillary angiomatosis. An approach to the identification of uncultured pathogens. N. Engl. J. Med. 323:1573-1580.

Ruoff, K. L., R. A. Whiley, and D. Beighton. 1999. *Streptococcus*, p. 283-296. In P. R. Murray, E. J. Baron, M. A. Pfaller, F. C. Tenover, and R. H. Yolken (ed.), Manual of Clinical Microbiology, 7th ed. ASM press, Washington, D.C.

Sakamoto, M, H. Hayashi, and Y. Benno. 2003. Terminal restriction fragment length polymorphism analysis for human fecal microbiota and its application for analysis of complex bifidobacterial communities. *Microbiol. Immunol.* 47(2):133-142.

Shin, J. H., F. S. Nolte, B. P. Holloway, and C. J. Morrison. 1999. Rapid identification of up to three *Candida* species in a single reaction tube by a 5' exonuclease assay using fluorescent DNA probes. J. Clin. Microbiol. 37:165-170.

Southern, E. M. 1979. Measurement of DNA length by gel electrophoresis. Anal. Biochem. 100:319-323.

Turenne, C. Y., E. Witwicki, D. J. Hoban, J. A. Karlowsky, and A. M. Kabani. 2000. Rapid identification of bacteria from positive blood cultures by fluorescence-based PCR-single-strand conformation polymorphism analysis of the 16S rRNA gene. J. Clin. Microbiol. 38:513-520.

Wellstood, S. A. 1987. Rapid, cost-effective identification of group A streptococci and enterococci by pyrrolidonyl-beta-naphthylamide hydrolysis. J. Clin. Microbiol. 25:1805-1806.

Widjojatmodjo, M. N., A. C. Fluit, and J. Verhoef. 1995. Molecular identification of bacteria by fluorescence-based PCR-single-strand conformation polymorphism analysis of the 16S rRNA gene. J. Clin. Microbiol. 33:2601-2606.

Woese, C. R. 1987. Bacterial evolution. Microbiol. Rev. 51:221-271.

* cited by examiner

RAPID IDENTIFICATION OF BACTERIA FROM POSITIVE BLOOD CULTURES

CROSS REFERENCE TO RELATED APPLICATIONS

This application claims priority under 35 USC §119(e) to U.S. Provisional Application Ser. No. 60/489,947, filed 24 Jul. 2003, the entirety of which is incorporated herein.

REFERENCE TO CITATIONS

Complete bibliographical citations to the documents identified by numbers in parenthesis in the text can be found in the Bibliography, immediately preceding the claims.

FIELD OF THE INVENTION

The present invention relates generally to a method of identifying bacteria in environmental and biological samples. More specifically, the invention is directed to a method of profiling bacteria and creating a bacteria profile database.

DESCRIPTION OF THE PRIOR ART

Detecting and identifying bacteria from the blood of patients is one of the most important roles of the clinical microbiology laboratory. The turn-around time for a positive result is critical because prompt and appropriate treatment of bloodstream infections reduces morbidity and mortality (9). Hospital-acquired infections (i.e., nosocomial infections) greatly increase health care costs due to the added expense associated with prolonged hospital stays and antimicrobial therapy (14). Over the past several decades, considerable effort has been expended on developing faster and more sensitive methods to detect bacteremia in clinical specimens. This effort has resulted in the availability of manual and automated systems that have good sensitivity for the initial detection of the most commonly encountered organisms that cause bacteremia.

One limitation that still remains in processing blood cultures is the requirement to subculture positive blood culture bottles in order to perform most biochemical or other tests needed for bacterial identification. This usually results in one or more days of delay during the identification process. In the interim, the patient is usually treated with a broad-spectrum antimicrobial agent which oftentimes proves unnecessary. Additionally, subcultures of fastidious organisms may fail to grow on solid media or there may be insufficient growth to allow identification and susceptibility testing with standard methods. These problems would be circumvented if rapid and accurate molecular methods were available for identifying bacteria directly from positive blood cultures.

A number of procedures have been reported to be successful in directly identifying the more commonly encountered bacteria in positive blood cultures. Early reports involved biochemical or immunologic methods to identify common agents of bacteremia such as staphylococci, streptococci, and enterococci (4, 8, 12, 26, 33). The primary disadvantage of these approaches is the inability to identify organisms less commonly encountered. This is especially problematic for laboratories serving populations that include significant numbers of immunosuppressed patients. More recently, methods such as fluorescent in-situ hybridization (24), vibrational spectroscopy (20), single-strand conformation polymorphism (SSCP) analysis of the 16S rRNA gene (32, 34), and sequence-based methods have been described (7, 10, 25). In general these methods have the advantage of allowing identification of a broader spectrum of pathogens and have the potential to be at least partially automated in the clinical laboratory.

SUMMARY OF THE INVENTION

The present invention is directed to terminal restriction fragment length polymorphism (T-RFLP) analysis for identifying bacteria relevant to blood infections. To date, the most commonly described use of T-RFLP is for systematic comparative community analyses of environmental samples (15, 21, 22). An early report, however, describes identifying clinical strains of Mycobacterium (2).

The present invention extends the utility of the T-RFLP technique by: 1) incorporating more than one fluorescent primer in each polymerase chain reaction (PCR); 2) using two non-overlapping primer sets to amplify a total of about 1300 bases of the 16S rRNA gene; and 3) developing a searchable terminal restriction fragment profile database (TRFPD) populated with 101 experimentally determined TRF profiles and an additional 5899 profiles predicted from 16S rDNA sequence data.

The invention further provides a rapid approach to species identification through the use of T-RFLP. Due to 16S rDNA sequence diversity among bacteria species, T-RFLP allows the rapid identification of bacterial pathogens directly from a positive blood culture. A Terminal Restriction Fragment (TRF) profile was created for each bacterial organism by sizing fragments from restriction digests of PCR products derived from two sets of 16S rDNA-specific fluorescent dye-labeled primers.

The invention further provides a method of creating and cataloging a TRF profile in a TRFP database containing 5899 predicted TRF profiles from sequence information representing 2860 different bacterial species. TRF profiles were experimentally determined for 69 reference organisms and 32 clinical isolates and compared against the predicted profiles in the TRFP database. The predictive value of the profiles was found to be accurate to the species level with most organisms tested. In addition, identification of 10 different genera was possible with profiles comprising two or three TRF's.

The ability to identify bacteria from blood cultures rapidly has the potential to reduce unnecessary use of broad-spectrum antibiotics, thereby preventing the development of antibiotic resistant bacteria, a growing problem in the health care industry, as well as to promote more timely prescription of appropriate antibiotics, thereby reducing the recovery time of bacteria infected patients and lowering costs.

The identification method described herein teaches the use of TRF profiling for identification of bacteria. The primary advantage of this method is the use of 16S rDNA-specific PCR primer sets, restriction digest combinations, and sizing of the resulting TRF to develop and validate a procedure for identifying bacteria from blood cultures. At its heart, amplicons generated from sample DNA using 16s rDNA-specific primers are compared to a reference database of corresponding amplicons from a very large plurality of different bacterial species. If the fragment length profile from the sample rDNA matches a profile contained in the database, the bacteria in the sample is quickly determined. A larger plurality of bacterial organisms were first subjected to PCR using 16s rDNA-specific primers. The results fragment length profile of the resulting amplicons was then stored in a TRFP database. The database can be searched and compared against incoming samples based on fragment length similarity and frequency of each profile. The TRF profiles represent a highly reproducible and predictive source for identifying a host of organisms associated with bacteremia.

With the present invention, bacterial identification can be obtained directly from positive blood bottles, without any intervening sub-culturing step. This eliminates the significant delays encountered in the conventional approach which requires isolated, sub-cultured colonies to identify the type of bacteria causing the bacteremia. Commercially available biochemical systems that require isolation of a microorganism after growth in a blood culture bottle generally require an additional 1–3 days before organism identification can be completed. In contrast, analysis of 16S rRNA genes by TRF profiling allows the identification process to be completed within approximately 8 hours after obtaining a positive blood bottle sample.

The present invention is readily adapted to 96-well templates for DNA extraction, PCR, restriction digestion, and capillary based fragment analysis (including TRF calculations and predictive scoring). The modular nature of the TRF procedure allows it to be adapted as necessary to primer set and restriction enzyme combinations as desired. For example, primer sets with specificity to fungi or enteric bacteria could be included to diversify and clarify the identification capability of the current procedure.

When an organism is identified, even if it must be tested further to determine which antibiotic will most efficiently and effectively kill it, knowing the genus or species of the infecting bacteria is highly useful. As knowledge of the various infecting bacteria is accumulated, it allows a clinician to compile a database of effective empiric therapies. In short, the physician can prescribe appropriate antibiotics to the patient based on accumulated empirical evidence. In addition, susceptibility testing can be adapted and applied directly to inoculations of cultures from positive blood culture bottles (without sub-culturing), thereby decreasing the time required to determine antibiotic susceptibilities once the organism has been identified by TRF profiling. Reducing the time needed to make a positive identification yields a host of benefits: it decreases the duration of infection (because appropriate treatment is begun earlier in the infection), it decreases the cost of patient care (because complications are lessened or eliminated entirely), it decreases the length of hospitalization, it decreases the development of broad-spectrum antibiotic resistance (because an appropriate antibacterial agent is used from the outset), and it decreases the mortality due to bacteremia. Thus, the real-world benefits and utility of the present invention are many.

Further objects and advantages of the invention will appear more fully from the following detailed description of the preferred embodiment of the invention made in conjunction with the accompanying drawings.

BRIEF DESCRIPTION OF THE DRAWINGS

FIG. 3 is a series of electropherograms for several organisms relevant to bacteremia. The X-axis present fragment size (in base pairs); the Y-axis presents fluorescent signal.

DETAILED DESCRIPTION OF THE INVENTION

Figure 1:
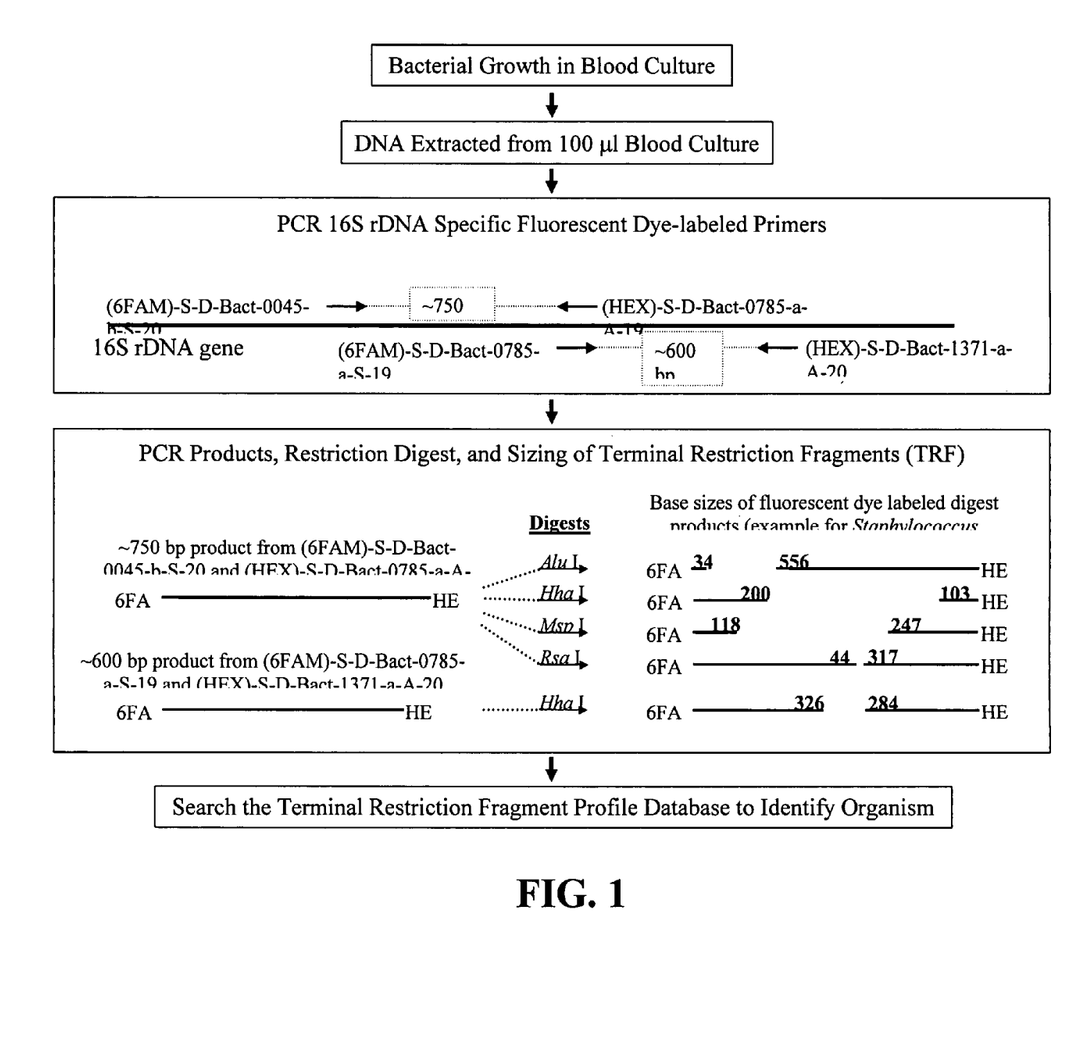
FIG. 1 is a flowchart outlining the procedure for generating TRF profiles.

Materials and Methods:

The procedure for identifying bacteria using TRF profiles is diagrammed in FIG. 1. As shown in FIG. 1, blood samples are first cultured in conventional fashion to allow any bacteria present in the samples to multiply. A 100 μl aliquot is then taken from each sample and the DNA extracted from each aliquot in conventional and well-known fashion. The extracted DNA is then subjected to PCR amplification using at least two different pairs of 16S rDNA-specific primers. At least one individual primer of each primer pair is labeled, preferably with a fluorescent label. In the preferred method, both primer in each primer pair is labeled with a differentially-detectable label. As shown in FIG. 1, the fluorophores 6-FAM and HEX are used (see the Examples). Any pair of differentially detectable labels will suffice. A host of suitable fluorophores for use in labeling PCR primers can be obtained commercially from Molecular Probes, Eugene, Oreg.

Once obtained, the amplified fragments (i.e., the amplicons) are sub-divided into smaller aliquots and each aliquot is digested with a different type of restriction endonuclease. As shown in FIG. 1, the endonucleases employed are Alu I, Hha I, Msp I, and Rsa I. These four endonucleases are simply representative examples. Any restriction endonuclease, now known or discovered or developed in the future, may be used in the present invention. By way of a non-limiting list, the following restriction endonucleases can all be purchased commercially from several national and international suppliers: Aat II, AccI, AccI11, Acc65 I, AccB7 I, Acy I, Age 1, Alu 1, A/w26 I, A/w441, Apa 1, Ava I, Ava 1I, Ba/I, BamH 1, Ban I, Ban II, Bbu 1, Bc/I, Bgl 1, Bg/1l, BsaM I, BsaO I, Bsp1286 I, BsrBR I, BsrS I, BssH II, Bst71 I, Bst98 I, Bst E II, Bst O I, Bst X I, Bst Z I, Bsu36 I, Cfo I, Cla 1, Csp I, Csp 45 I, Dde I, Dpn I, Dra 1, EclHK I, Eco47 III, Eco52 I, Eco72 I, EcoI CR I, EcoR I, EcoR II EcoR V, Fok I, Hae 11, Hae1I1, Hha I, Hinc II, Hind III, Hinf I, Hpa I, Hpa II, Hsp92 I, Hsp92 II, I-Ppo I, Kpn I, Mbo I, Mbo II, Mlu 1, Msp I, MspA I, Nae 1, Nar, Nci I, Nco I, Nde 1. NgoM I, Nhe I, Not I, Nru I, Nsi 1, Pst 1, Pvu 1, Rvu II, Rsa 1, Sac I, Sac II, Sal 1, Sau3A I, Sau96 I, Sca 1, Sfi I, Sgf I, Sin I, Sma 1, SnaB I, Spe 1, Sph I, Ssp 1, Sst I, Stu 1, Sty 1, Taq I, Tru9 I, Tth111 I, Vsp I, Xba I, Xho I, Xho II, Xma 1, and Xmn I.

The restriction fragments are then size-sorted to yield a restriction fragment length profile. The restriction fragments can be size-sorted by any means now known in the art or developed in the future for separating nucleic acid fragments based on molecular weight. Gel or capillary electrophoresis is the preferred method of size-sorting the restriction fragments.

Restriction fragment length profiles are generated in this fashion for a host of bacterial strains and the data compiled into a searchable database. The restriction fragment length profiles generated directly from a positive blood culture are then compared to the profiles stored in the database. In this fashion, blood cultures that test positive for bacteria can be subjected to the invention and the infecting bacteria quickly identified.

Bacterial Strains:

Referring to Table 1, below, 69 reference organisms and 32 clinical blood isolates were analyzed by TRF profiling. The 69 reference organisms presented in Table 1 include 40 of the most common bacterial species isolated from positive blood cultures. The BacT/Alert blood culturing system (Organon Teknika Corp., Durham, N.C.) was used to perform Gram staining for all positive blood cultures. All reference organisms and positive blood bottles were cultured on trypticase soy—5% sheep blood or chocolate agar at 37° C. under the appropriate atmospheric conditions. Blood bottle isolates were identified using the automated Vitek system (bioMérieux Vitek Inc., Hazelwood, Mo.) using standard biochemical methods.

TABLE 1

Bacterial strains analyzed by TRF profiling

| Species | Strain[a] |
|---|---|
| Acinetobacter baumannii | ATCC 19606 |
| Acinetobacter calcoaceticus | MC 143 |
| Acinetobacter lwoffii | ATCC 17925 |
| Actinomyces pyogenes | MC 32R |
| Aeromonas hydrophila | ATCC 35654 |
| Bacillus sp. | MC 95 |
| Bacteroides distasonis | ATCC 8503 |
| Bacteroides fragilis | ATCC 25285; MC 147 |
| Bacteroides thetaiotaomicron | ATCC 29741 |
| Bacteroides uniformis | MC 124 |
| Bacteroides vulgatus | ATCC 8482 |
| Bartonella elizabethae | MC 71R |
| Bartonella henselae | MC 72R |
| Bifidobacterium sp. | MC 103 |
| Bordetella parapertussis | MC 38R |
| Bordetella pertussis | MC 13R |
| Campylobacter jejuni | ATCC 43443 |
| Citrobacter freundii | MC 86; MC 164 |
| Clostridium perfringens | ATCC 13124 |
| Corynebacterium ammoniagenes | ATCC 6871 |
| Corynebacterium diphtheriae | MC 41R |
| Corynebacterium jeikeium | ATCC 43734 |
| Corynebacterium kutscheri | ATCC 11036 |
| Corynebacterium pseudodiphtheriticum | ATCC 10700 |
| Enterobacter cloacae | ATCC 23355; MC 115; MC 165 |
| Enterobacter gergoviae | MC 162 |
| Enterococcus faecalis | ATCC 29212; ATCC 51299; MC 87; MC 120 |
| Enterococcus hirae | MC 149 |
| Enterobacter sp. | MC 138 |
| Escherichia coli | ATCC 11229; ATCC 25922; ATCC 35150; ATCC 35218; PS 0111; MC 16R |
| Fusobacterium nucleatum | MC 49R |
| Haemophilus influenzae | ATCC 9006; ATCC 49247; MC 50R |
| Haemophilus parainfluenzae | MC 17R |
| Haemophilus somnus | ATCC 43625 |
| Klebsiella pneumoniae | ATCC 13883; ATCC 700603; MC 134 |
| Leifsonia aquaticum | ATCC 51721 |
| Lactobacillus fermentum | ATCC 9338 |
| Legionella micdadei | MC 19R |
| Listeria monocytogenes | ATCC 91915 |
| Listeria sp. | MC 128 |
| Micrococcus luteus | ATCC 4698 |
| Moraxella catarrhalis | ATCC 25238 |
| Moraxella osloensis | MC 113 |
| Neisseria gonorrhoeae | ATCC 49226 |
| Neisseria meningitidis | ATCC 13102 |
| Neisseria sp. | MC 140 |
| Peptostreptococcus anaerobius | ATCC 27337 |

TABLE 1-continued

Bacterial strains analyzed by TRF profiling

| Species | Strain[a] |
|---|---|
| Peptostreptococcus asaccharolyticus | MC 56R |
| Proteus mirabilis | ATCC 7002; MC 109; MC 166 |
| Pseudomonas aeruginosa | MC 126; MC 151 |
| Rhodococcus equi | ATCC 6939; MC 59R |
| Salmonella abaetetuba | ATCC 35640 |
| Salmonella enteritidis | MC 24R |
| Serratia marcescens | MC 93; MC 159 |
| Staphylococcus aureus | ATCC 6538; ATCC 25923; ATCC 29213; ATCC 33862; ATCC 43300; MC 53R; MC 91; MC 97R; MC 98R; MC 99R; MC 100R |
| Staphylococcus epidermidis | ATCC 35983 |
| Staphylococcus haemolyticus | ATCC 29970 |
| Staphylococcus saprophyticus | MC 28R |
| Stenotrophomonas maltophilia | ATCC 13637 |
| Streptococcus pneumoniae | ATCC 49619; MC 63R; MC 132; MC 167 |
| Streptococcus sp. | MC 12R; MC 104; MC 105; MC 111; MC 153; MC 169 |
| Yersinia sp. | MC 64R |

[a]ATCC, American Type Culture Collection; MC, Marshfield Clinic isolate

Minimum inhibitory concentrations (MIC) for *S. aureus* were determined by microbroth dilution (Vitek System, bioMérieux Inc.). Confirmation of oxacillin resistance was done using Mueller-Hinton agar with 4% sodium chloride and 6 µg/ml of oxacillin sodium. Isolates were considered methicillin-resistant if the MIC for oxacillin was greater than or equal to 4 µg/ml and growth was present on oxacillin confirmatory media.

DNA Extraction:

DNA was extracted from cultured colonies using a modification of the tissue protocol for the QIAmp DNA Mini Kit (Qiagen, Inc., Valencia, Calif.). A cell suspension (200 µL) in $H_2O$ (containing ~5–10 mg cells) was mixed with 200 µl of QIAmp Buffer AL and 10 µl of proteinase K (20 mg/ml). Samples were incubated for 15 min. at 56° C. and then for 15 min. at 95° C. EtOH (200 µl) was added and mixed by vortexing. The samples were loaded, washed, and eluted in 200 µl from QIAmp spin columns as indicated in the remainder of the manufacturer's protocol.

DNA was extracted from growth-positive blood culture bottles using a modification of the QIAmp DNA Mini Kit Tissue protocol and incorporating a benzyl alcohol extraction (11). Blood culture (100 µl aliquot) was mixed with 100 µl of QIAmp Buffer AL and 10 µl of proteinase K (20 mg/ml). Samples were incubated for 15 min. at 56° C. and then for 15 min. at 95° C. Samples were then diluted with 600 µl of filter sterile $H_2O$ to reduce the viscosity. Benzyl alcohol (500 µl) was added to each sample, mixed by vortexing for 10 sec., and centrifuged at 20,000×g for 5 min. A 400 µl aliquot of the aqueous supernatant was transferred to a new 1.5 ml tube and 200 µl of EtOH was added and the solution mixed by vortexing. Samples were loaded, washed, and eluted in 200 µl buffer from QIAmp spin columns as indicated in the remainder of the manufacturer's protocol.

PCR Primers:

Independent reactions with two sets of fluorescent labeled primers targeting the 16S rRNA gene were used for PCR. Amplifications were performed on chromosomal preparations from reference strains, as well as on the DNA from blood isolates.

The primers were chosen based on previously published evaluations of domain specificity (1, 5, 6, 27, 35) and maximization of matches received from queries using the T-RFLP analysis program (TAP T-RFLP) of the Ribosomal Database Project-II (19). Including a C or T at the third position from 3' in (6FAM)-S-D-Bact-0045-b-S-20 was predicted to enhance annealing to the streptococci and closely related organisms. As indicated, primers were labeled at the 5' end with the dyes 6-carboxyfluorescein (6-FAM), 4,7,2', 4',5',7'-hexachloro-6-carboxyfluorescein (HEX), or N,N,N', N'-tetramethyl-6-carboxyrhodamine (TAMRA). Other suitable fluorophores can be obtained commercially from Molecular Probes. All primers were purchased from Sigma-Genosys (The Woodlands, Tex.).

The 5' region (encompassing hypervariable regions V1–V3) of the 16S rRNA gene was amplified with S-D-Bact-0045-b-S-20 (5'-6FAM-GCY TAA CAC ATG CAA GTY GA) (SEQ. ID. NO: 1) and S-D-Bact-0785-a-A-19 (5'-HEX-CTA CCA GGG TAT CTA ATC C) (SEQ. ID. NO: 2). The 3' region of the 16S rRNA gene was amplified with S-D-Bact-0785-a-S-19 (5'-6FAM-GGA TTA GAT ACC CTG GTA G) (SEQ. ID. NO: 3) and S-D-Bact-1371-a-A-20 (5'-HEX-AGG CCC GGG AAC GTA TTC AC) (SEQ. ID. NO: 4). PCR products from the primer pairs were predicted to be ~750 bp and ~600 bp, respectively, with some variability dependent on the organism from which the template DNA is extracted.

The primers for detection of nuc, referred to here as TAMRA-nuc-S (5'-TAMRA-GCG ATT GAT GGT GAT ACG GTT) (SEQ. ID. NO: 5) and nuc-A (5'-AGC CAA GCC TTG ACG AAC TAA AGC) (SEQ. ID. NO: 6), were reported previously and correlated with coagulase phenotype in staphylococci (3, 17, 18). The predicted PCR product from the targeted template was 279 bp in length and did not contain an Hha I restriction site.

Primers for detection of the mecA gene of staphylococci, referred to here as TAMRA-mecA-S (5'-TAMRA-AAA ATC GAT GGT AAA GGT TGG C) (SEQ. ID. NO: 7) and mecA-A (5'-AGT TCT GCA GTA CCG GAT TTG C) (SEQ. ID. NO: 8), were previously reported and evaluated for accuracy of identification of methicillin resistance in staphylococci (18, 23). The predicted PCR product from the targeted template was 530 or 533 bp in length and contains an Hha I restriction site, resulting in a TAMRA labeled fragment of 331 or 334 bases, respectively. The PCR amplification of the 3' region of the 16S rRNA gene (6-FAM labeled S-D-Bact-0785-a-S-19 and HEX labeled S-D-Bact-1371-a-A-20), nuc, and mecA were accomplished in a triplex reaction, similar to previous reports (16, 18), under conditions described below.

Controls for terminal fragment size and restriction digest were prepared using TAMRA labeled S-D-Bact-0785-a-A-19 (5'-TAMRA-CTA CCA GGG TAT CTA ATC C) (SEQ. ID. NO: 9) and unlabelled S-D-Bact-0045-b-S-20 (5'-GCY TAA CAC ATG CAA GTY GA) (SEQ. ID. NO: 10). PCR was performed with chromosomal DNA preparations from four organisms (*Haemophilus influenzae*, *Micrococcus luteus*, *Salmonella enteritidis*, and *Stenotrophomonas maltophilia*) for which the TRF sizes of the TAMRA labeled products were known for each restriction enzyme (Alu I, Hha I, Msp I, and Rsa I).

PCR Conditions:

The reaction mixtures for PCR contained 1×PCR buffer, 200 µM each deoxynucleoside triphosphate, 3.0 mM MgCl$_2$, 0.5 µM each primer species, 1.0 U Taq DNA polymerase, and 1.0 µl chromosomal preparation per 15 µl reaction. Due to approximately 4-fold higher detection sensitivity of the fluorescence emission from the 6FAM dye relative to HEX dye, a ratio of 1 part 6FAM-labeled primer (0.125 µM) to 3 parts unlabelled primer (0.375 µM) was used for primers S-D-Bact-0045-b-S-20 and S-D-Bact-0785-a-S-19. DNA was amplified using a model 9600 thermal cycler (Perkin-Elmer, Norwalk, Conn.) with the following program: 15 min at 94° C. for denaturation and Taq activation, 35 cycles consisting of denaturation (45 s at 94° C.), annealing (30 s at 52° C.), extension (60 s at 72° C.), and a final extension for 5 min at 72° C.

Thermal gradient PCR with various magnesium concentrations was performed with reference strains to determine conditions that provided optimal product formation with minimal non-specific products. All PCR reactions were analyzed by gel electrophoresis and stained with ethidium bromide (EtBr) to assure product formation prior to restriction digest.

Restriction Digests of PCR Products:

PCR products were digested with restriction enzymes (Invitrogen, Carlsbad, Calif. and New England BioLabs, Beverly, Mass.) without further purification. Each 10 µl restriction digest contained 1 µl of PCR product, 0.5 µl of restriction enzyme, and 8.5 µl of prepared stock containing 2.5 ng/µl each appropriate size/digest control DNA in 1× buffer. The PCR product of 6-FAM labeled S-D-Bact-0045-b-S-20 and HEX labeled S-D-Bact-0785-a-A-19 (amplifying the 5' region of the 16S rRNA gene) was digested in separate reactions with Alu I (5'-AG↓CT-3'), Hha I (5'-GCG↓C-3'), Msp I(5'-C↓CGG-3'), and Rsa I (5'-GT↓AC-3'). The PCR product of 6-FAM labeled S-D-Bact-0785-a-S-19 and HEX labeled S-D-Bact-1371-a-A-20 (amplifying the 3' region of the 16S rRNA gene), or the product(s) of the triplex reaction, were only digested with Hha I. Restriction digests were incubated for 2 hr at 37° C. followed by 20 min at 65° C. for enzyme inactivation.

16S rDNA Terminal Restriction Fragment Length Analysis:

The lengths of TRFs derived from amplified DNA products were determined by electrophoresis with a model 377 automated sequencer (Applied Biosystems, Foster City, Calif.). Samples were prepared by combining 2.0 µl of restriction digest product, 2.5 µl of deionized formamide, 0.5 µl of 25 mM EDTA (pH 8.0) containing 5% (wt/vol) blue dextran, and 0.50 µl of X-rhodamine MapMarker 1000 XL (BioVenture, Inc., Murfreesboro, Tenn.). The size standard contains single strands of DNA with a single ROX fluorophore at 50, 75, 100, 125, 150, 200, 250, 300, 350, 400, 450, 475, 500, 550, 600, 650, 700, 750, 800, 850, 900, 950, and 1000 bases. Samples were mixed by pipeting, denatured at 94° C., and immediately cooled to 4° C. Aliquots of 1.0 µl were loaded to a 36 cm, 4.75% denaturing polyacrylamide gel and electrophoresed at 51° C. for 4.0 hr with limits of 3 kV and 60 mA. Data was collected using GeneScan®-brand software (Applied Biosystems) and the lengths of control and sample TRFs were calculated by comparison with the internal standard using the Local Southern method (31). Fragments lengths ≧20 nts but <50 nts were calculated by linear extrapolation from the migration times of the 50 and 75 base standards.

Construction of the Terminal Restriction Fragment Profile Database (TRFLP):

A program and a searchable TRFP database were developed to support calculation and comparison, respectively, of raw data files containing 16S rDNA gene TRF size information exported from the GeneScan® software. The program performs mean and standard deviation calculations of control fragment lengths, providing data for quality control from every sample lane. The maximum area 6-FAM and HEX peak data for each lane are identified and organized according to the respective primer set and restriction digest combination. The program is then used to compare the sample TRF profile, within an adjustable search window for each fragment, against organism profiles in the TRFP database. The results from a Gram stain can also be selected in the data input window to limit the search. The result of a search includes the number of matching fragment lengths (within chosen windows), ordering of closest matches, and links to best match TRF profiles.

Four raw data files containing TRF sizes extracted for bacterial sequences with individual primer and restriction enzyme combinations (described above) were obtained by special request from the Ribosomal Database Project II (RDP-II) (19). The search parameters chosen here allowed as many as 5 mismatches in the first 15 bases from the 5' end of each primer. The data for in silico digest products derived from each primer were combined and sorted by accession number or other unique identifier. The sorted data set was then cleared of all organism entries that did not have restriction digest information for each of the four 16S rDNA specific primers. The remaining profiles each contained 10 TRF's for 5899 organisms, representing 2860 unique species, and were used to populate the TRFP database.

RESULTS

Figure 2:
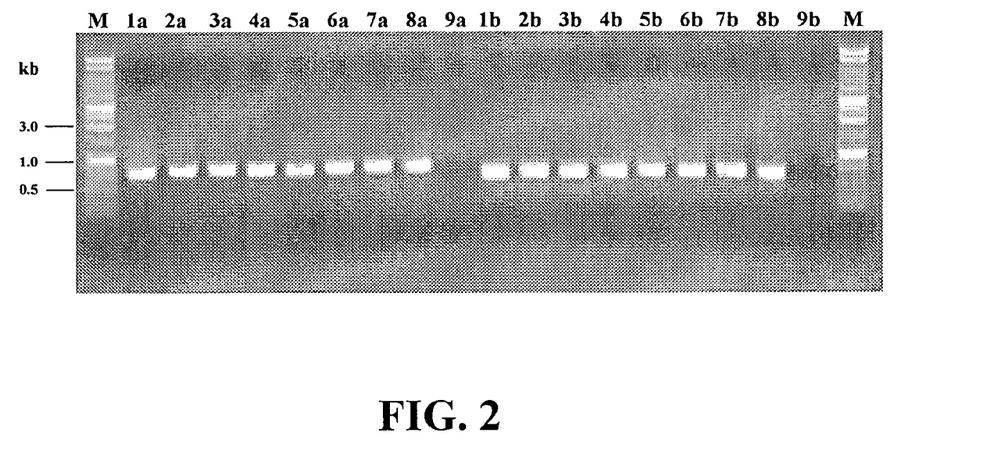
FIG. 2 is a gel electrophoresis photograph of representative PCR products from 16S rDNA-specific primers.
Figure 3A:
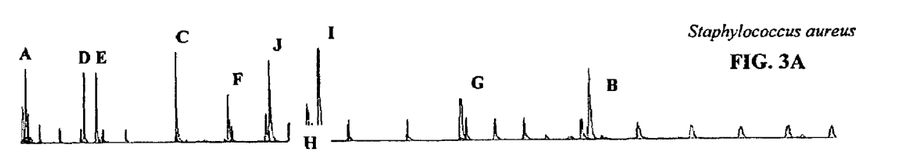
FIG. 3A shows *Staphylococcus aureus.
Figure 3B:
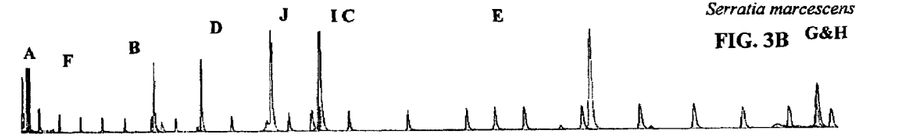
* FIG. 3B shows *Enterococcus faecalis.
Figure 3C:
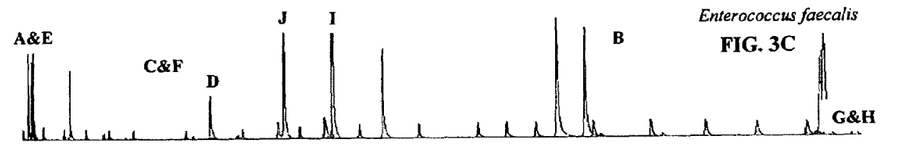
* FIG. 3C shows *Streptococcus pneu-moniae.
Figure 3D:
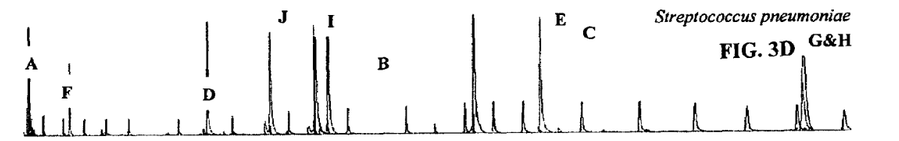
* FIG. 3D shows *Klebsiella pnemoniae.
Figure 3E:
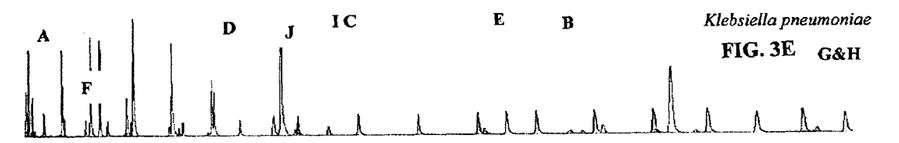
* FIG. 3E shows *Psuedomonas aeruginosa.
Figure 3F:
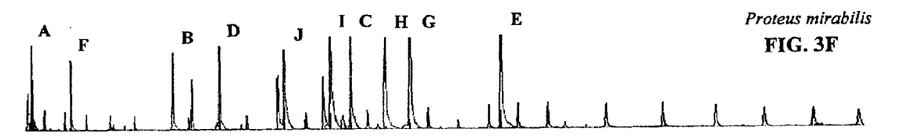
* FIG. 3F shows *Proteus mirabilis.
Figure 3G:
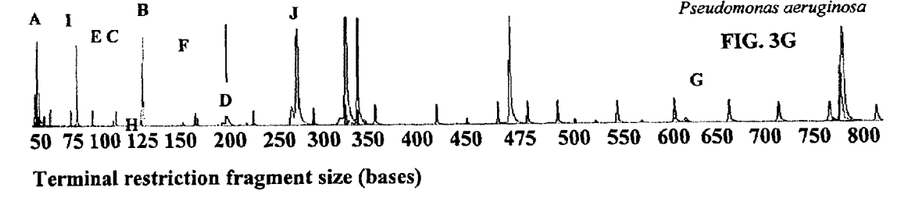
* and FIG. 3G shows *Serratia marcescens.*

PCR Products with 16S rDNA Specific Primers:

FIG. 2 illustrates the chromosomal preparations taken from the following organisms and which were subsequently used in PCR to generate reference profiles:

lanes 1a and 1b: *Escherichia coli* ATCC 35218
lanes 2a and 2b: *Enterococcus faecalis* ATCC 51299
lanes 3a and 3b: *Haemophilus influenzae* ATCC 49247
lanes 4a and 4b: *Klebsiella pneumoniae* ATCC 700603
lanes 5a and 5b: *Micrococcus luteus* ATCC 4698
lanes 6a and 6b: *Salmonella enteritidis* MC 24R
lanes 7a and 7b: *Staphylococcus aureus* ATCC 43300 and
lanes 8a and 8b: *Stenotrophomonas maltophilia* ATCC 13637.

Lanes 9a and 9b contain the PCR blanks and lanes M contain the molecular size markers (1 kb ladder, values to the left are kilobases). The letters with each lane number denote the primer pair used for PCR:

"a", (6FAM)-S-D-Bact-0045-b-S-20 and (HEX)-S-D-Bact-0785-a-A-19; and

"b", (6FAM)-S-D-Bact-0785-a-S-19 and (HEX)-S-D-Bact-1371-a-A-20.

The PCR products were separated in a 1.0% agarose gel at 120V for 20 min.

As shown in FIG. 2, the PCR products from (6FAM)-S-D-Bact-0045-b-S-20 and (HEX)-S-D-Bact-0785-a-A-19 were ~750 bp, while products from (6FAM)-S-D-Bact-0785-a-S-19 and (HEX)-S-D-Bact-1371-a-A-20 were ~600 bp. The DNA bands obtained from clinical isolates and their respective extractions from the positive blood culture bottles were indistinguishable.

TRF Digest/Size Controls:

Validation of TAMRA-labeled TRF control sizes, three fragments for each restriction digest, was performed by calculation from duplicate loads of triplicate digests done on two consecutive days (12 values for each control, data not shown). Under the conditions used for the restriction digests there were no detectable undigested TAMRA-labeled fragments in the sizing gels. The control values calculated for TAMA-labeled TRF sizes during determination of organism profiles are compiled in Table 2:

TABLE 2

Statistical evaluation of TAMRA-labeled TRF digest/size controls

| Digest and Control DNA | n | Expected Size[a] | Range | Mean | Std Dev |
|---|---|---|---|---|---|
| Alu I | | | | | |
| *St. maltophilia* ATCC 13637 | 152 | 69 | 68.4–69.9 | 68.6 | 0.28 |
| *M. luteus* ATCC 4698 | 152 | 226 | 224.8–226.4 | 225.3 | 0.18 |
| *S. enteritidis* MC 24R | 152 | 514 | 512.1–515.0 | 513.8 | 0.30 |
| Hha I | | | | | |
| *M. luteus* ATCC 4698 | 304 | 105 | 103.4–104.4 | 104.2 | 0.08 |
| *S. enteritidis* MC 24R | 304 | 228 | 226.4–227.8 | 227.2 | 0.11 |
| *St. maltophilia* ATCC 13637 | 304 | 425 | 423.0–425.4 | 424.2 | 0.17 |
| Msp I | | | | | |
| *S. enteritidis* MC 24R | 152 | 82 | 80.7–84.1 | 82.8 | 0.53 |
| *M. luteus* ATCC 4698 | 152 | 176 | 175.2–178.6 | 177.2 | 0.52 |
| *St. maltophilia* ATCC 13637 | 152 | 298 | 297.3–300.5 | 299.2 | 0.52 |
| Rsa I | | | | | |
| *H. influenzae* ATCC 49247 | 152 | 55 | 53.7–56.8 | 54.8 | 0.46 |
| *M. luteus* ATCC 4698 | 152 | 162 | 161.1–162.5 | 161.5 | 0.44 |
| *S. enteritidis* MC 24R | 152 | 369 | 368.2–369.7 | 369.0 | 0.46 |

[a]Expected control fragment sizes, following specified restriction digest, as determined by evaluation of 16S rRNA gene sequence information for each strain.

For TRF's to be included in the profile for a given organism, the three internal digest control sizes were required to fall within a ±3 base window for the expected size. Although only 5 of the mean TRF values rounded to exactly the expected size, all 12 control TRF's sizes were within 1 base of the expected value. The precision of fragment size determination is apparent from the range and standard deviation calculations, for which the greatest range was for two of the Msp I digest controls (3.4 bases). The average range for all the controls in this study, weighted for frequency, was ±1.1 base from the mean.

TRF Profiles for Reference Strains and Clinical Isolates:

The TRF profiles for 69 reference strains and 32 clinical isolates were determined and incorporated into the TRFP database. Combined with the original predicted TRF profiles there are currently a total of 2435 TRF profiles representing 921 different species of potential relevance to bacteremia. Representative composite electropherograms for several organisms relevant to bacteremia are presented in FIGS. 3A–3G.

FIGS. 3A–3G illustrate TRF profiles for several strains isolated from positive blood culture bottles. Each panel is a compilation of the five PCR product/restriction digest electropherograms for each organism and the applicable range of the standard curve (50–800 bases). The single major 6FAM fragments and HEX fragments of each digest are identified by letters (A–J). TRF's derived from PCR products of (6FAM)-S-D-Bact-0045-b-S-20 and (HEX)-S-D-Bact-0785-a-A-19 are identified by A and B (Alu I), C and D (Hha I), E and F (Msp I), or G and H (Rsa I), respectively. TRF's derived from PCR products of (6FAM)-S-D-Bact-0785-a-S-19 and (HEX)-S-D-Bact-1371-a-A-20 are identified by I and J (Hha I), respectively. Tabulated fragment size information for each organism is available from Table 3.

TABLE 3

TRF profiles for reference and clinical isolates compared to sequence predicted TRF profiles.

| Organism[a] | Tested Isolates | Alu I[b] 6FAM | HEX | Hha I[b] 6FAM | HEX | Msp I[b] 6FAM | HEX | Rsa I[b] 6FAM | HEX | Hha I[c] 6FAM | HEX | Predicted Profiles[d] | Matches[e] 10/10 | 9/10 |
|---|---|---|---|---|---|---|---|---|---|---|---|---|---|---|
| Staphylococcus aureus | 11 | 34 | 556 | 200 | 103 | 118 | 247 | 448 | 317 | 326 | 284 | 10 | 10 | — |
| Staphylococcus epidermidis | 1 | 34 | 556 | 200 | 103 | 118 | 247 | 449 | 317 | 326 | 284 | 5 | 4 | 1 |
| Staphylococcus haemolyticus | 1 | 34 | 556 | 200 | 104 | 117 | 247 | 449 | 317 | 326 | 284 | 3 | 3 | — |
| Staphylococcus saprophyticus | 1 | 35 | 556 | 200 | 104 | 117 | 247 | 449 | 317 | 326 | 284 | 3 | 2 | 1 |
| Escherichia coli | 6 | 34 | 153 | 336 | 227 | 458 | 82 | 389 | 370 | 324 | 148 | 37 | 36 | 1 |
| Enterococcus faecalis | 4 | 38; 220 | 557 | 179 | 223 | 35; 530 | 179 | UD | UD | 324 | 284 | 4 | 4 | — |
| Streptococcus, group A | 1 | 121 | 369 | 545 | 222 | 520 | 82 | 594 | 173 | 325 | 284 | f, h | 4 | 6 |
| Streptococcus, group B | 2 | 121 | 369 | 544 | 222 | 520 | 82 | 594 | 172 | 325 | 284 | f, h | 4 | 6 |
| Streptococcus, group F | 1 | 129 | 369 | 552 | 222 | 528 | 82 | 456 | 316 | 325 | 284 | f, j | — | 1 |
| Streptococcus, group G | 1 | 121 | 369 | 544 | 222 | 41 | 82 | 593 | 172 | 325 | 284 | f, k | 4 | 4 |
| Streptococcus, viridans group | 1 | 34 | 369 | 544 | 222 | 520 | 82 | 594 | 172 | 325 | 284 | f, m | — | 6 |
| Streptococcus pneumoniae | 4 | 33 | 369 | 543 | 222 | 518 | 82 | UD | UD | 325 | 284 | 2 | 2 | — |
| Klebsiella pneumoniae | 3 | 34 | 514 | 334 | 227 | 458 | 82 | 387; UD | 370; UD | 324 | 285 | 9 | 9 | — |
| Pseudomonas aeruginosa | 2 | 33 | 152 | 116 | 226 | 106 | 190 | 609 | 145 | 72 | 285 | 7 | 6 | — |
| Bacteroides fragilis | 2 | 37 | 67 | 61 | 419 | 58 | 248 | 614 | 146 | 320 | 23 | 18 | 18 | — |
| Proteus mirabilis | 3 | 35 | 185 | 336 | 227 | 460 | 82 | 390 | 370 | 324 | 286 | g | — | — |
| Serratia marcescens | 2 | 35 | 152 | 336 | 227 | 460 | 82 | UD | UD | 324 | 285 | 8 | 7 | 1 |
| Micrococcus luteus | 1 | 32 | 225 | 634 | 104 | 126 | 177 | 419 | 161 | 70 | 286 | 3 | — | 3 |
| Clostridium perfringens | 1 | 201 | 345 | 194 | 539 | 486 | 187 | 415 | 317 | 322 | 283 | 3 | 3 | — |
| Citrobacter freundii | 2 | 35 | 514 | 336 | 228 | 460 | 82 | 389 | 370 | 324 | 285 | 3 | 2 | — |
| Acinetobacter baumannii | 1 | 33 | 153 | 169 | 587 | 45 | 299 | 720 | 43 | 72 | 285 | 3 | 3 | — |
| Salmonella enteritidis | 1 | 35 | 514 | 335 | 227 | 460 | 82 | 389 | 370 | 324 | 148 | 2 | 1 | 1 |
| Aeromonas hydrophila | 1 | 36 | 152 | 176 | 228 | 51 | 82 | UD | UD | 324 | 99 | 9 | 7 | 1 |
| Coryn. pseudo-diphtheriticum | 1 | 194 | 186 | 329 | 104 | 124 | 247 | 41 | 146 | 39 | 137 | 2 | 2 | — |
| Enterobacter cloacae | 3 | 35 | 514 | 335 | 227 | 459 | 82 | 389; UD | 370; UD | 324 | 148 | 2 | 2 | — |
| Rhodococcus equi | 2 | 133 | 174 | 630 | 104 | 124 | 82 | 40 | 146 | 39 | 261 | 3 | 2 | — |
| Bartonella henselae | 1 | 173 | 344 | 24 | 227 | 371 | 299 | UD | UD | 71 | 282 | 5 | — | 5 |
| Bordetella pertussis | 1 | 196 | 514 | 531 | 223 | 454 | 156 | 436 | 318 | 71 | 279 | 2 | 1 | 1 |
| Campylobacter jejuni | 1 | 27 | 532 | 58 | 40 | 432 | 298 | 416 | 317 | 328 | 284 | 3 | 2 | 1 |
| Enterococcus hirae | 1 | 38 | 557 | 179 | 223 | 35 | 179 | UD | UD | 324 | 284 | 3 | 3 | — |
| Listeria monocytogenes | 1 | 34 | 557 | 147 | 40 | 109 | 179 | 398 | 369 | 324 | 282 | 2 | 2 | — |

TABLE 3-continued

TRF profiles for reference and clinical isolates compared to sequence predicted TRF profiles.

| Organism[a] | Tested Isolates | Alu I[b] 6FAM | HEX | Hha I[b] 6FAM | HEX | Msp I[b] 6FAM | HEX | Rsa I[b] 6FAM | HEX | Hha I[c] 6FAM | HEX | Predicted Profiles[d] | Matches[e] 10/10 | 9/10 |
|---|---|---|---|---|---|---|---|---|---|---|---|---|---|---|
| *Moraxella osloensis* | 1 | 33 | 67 | 155 | 597 | 263 | 190 | UD | UD | 72 | 286 | 2 | 2 | — |
| *Neisseria gonorrhoeae* | 1 | 35 | 556 | 174 | 224 | 90 | 178 | 86 | 317 | 324 | 284 | 2 | 1 | 1 |

UD: Undigested PCR product (6FAM and HEX fragment sizes were both >700 bases).
[a]Organisms are presented in approximate order of incidence for isolation from blood culture at Marshfield Laboratories. With the exception of the *streptococci*, the experimental data for organisms in Table 3 were included only when at least two or more profiles were available for either experimental or sequence predicted data.
[b]Labeled fragments derived from the PCR product of (6FAM)-S-D-Bact-0045-b-S-20 and (HEX)-S-D-Bact-0785-a-A-19.
[c]Labeled fragments derived from the PCR product of (6FAM)-S-D-Bact-0785-a-S-19 and (HEX)-S-D-Bact-1371-a-A-20.
[d]The predicted profiles were derived for organisms with complete 16S rDNA sequence information as determined by a data extraction provided through the RDP-II (19).
[e]The number of sequence predicted profiles in the TRFPD that match distinct fragment sizes from the experimentally determined profiles within a ±3 base window.
[f]Species of the clinical isolates of streptococci were not determined.
[g]Information derived from sequence data did not allow determination of a complete sequence predicted TRF profile.
[h]Experimental profiles matched 10 out of 10 for *S. agalactiae* (2/2) and *S. suis* (2/2), 9 out of 10 matches for *S. dysgalactiae* (3/3) *S. oralis* (1/1), *S. parasanguinis* (1/1), and *S. pyogenes* (1/2).
[j]Experimental profile matched 9 out of 10 for *S. constellatus* (1/1).
[k]Experimental profiles matched 10 out of 10 for *S. dysgalactiae* (3/3) and *S. pyogenes* (1/2), 9 out of 10 matches for *S. agalactiae* (2/2) and *S. suis* (2/2).
[m]Experimental profile matched 9 out of 10 for *S. agalactiae* (2/2), *S. oralis* (1/1), *S. parasanguinis* (1/1), and *S. suis* (2/2).

The 33 experimentally determined TRF profiles in Table 3 are presented in the approximate order of incidence for isolation at Marshfield Laboratories. For any given organism, all fragment sizes initially within a 3-base range were averaged and rounded to the nearest base to derive the reported cumulative TRF profiles (as with *S. aureus* and *E. coli*). When an experimental TRF was >3 bases different than a duplicate, or another TRF from the same species, the entire procedure from the initial PCR was repeated for that isolate to confirm or correct the sizing of a fragment. As a result, the TRF's derived from products of (6FAM)-S-D-Bact-0045-b-S-20 and (HEX)-S-D-Bact-0785-a-A-19 for four different *E. faecalis* strains were found to have reproducible size diversity for two of the TRF's (6FAM fragment with Alu I and Msp I). In contrast, all of the staphylococcal species have essentially the same TRF profile and classification is described in a later section. The majority of the experimentally determined TRF profiles matched with the sequence predicted TRF profiles for the same species.

Accurate identification of organisms at the genus level was successful through searches using partial TRF profiles as shown in Table 4. Note the readily apparent correspondence between all three of FIGS. 4A, 4B, and 4C, all of which are from bacteria of the genus *Staphylococcus*.

For further example, all 84 staphylococcal profiles in the TRFP database match one of two minimal TRF profiles containing a 200±3 (81/84) (FIG. 3A, *S. aureus*, Peak C) or 539±3 (3/84) base TRF derived from (6FAM)-S-D-Bact-0045-b-S-20 and a 104 base TRF (FIG. 3A, *S. aureus*, Peak D) derived from (HEX)-S-D-Bact-0785-a-A-19 digested with Hha I, without any matches for another genus. In addition, 96% of the corynebacteria and rhodococci (124/129) matched a profile containing only 2 TRF's with only 2 other organisms from any other genus (*Brevibacterium helvolum* and *Tropheryma whippelii*).

TABLE 4

Genus specificity of partial TRF profiles for blood pathogens

| Organisms[a] | Alu I[b] 6FAM | HEX | Hha I[b] 6FAM | HEX | Msp I[b] 6FAM | HEX | Rsa I[b] 6FAM | HEX | Hha I[c] 6FAM | HEX | Species | Genus profiles[d] | Same genus matches | Different genus matches |
|---|---|---|---|---|---|---|---|---|---|---|---|---|---|---|
| *Staphylococcus* | — | — | 200; 539 | 104 | — | — | — | — | — | — | 37 | 84 | 84 | 0 |
| *Enterococcus* | — | — | 180 | 224 | — | — | — | — | — | — | 17 | 46 | 44 | 1[e] |
| *Streptococcus* | — | — | 543; 552 | 222 | — | — | — | — | — | — | 28 | 49 | 45 | 1[f] |
| *Bacteroides* | — | 68 | — | — | — | 247 | — | — | 319 | — | 10 | 54 | 44 | 3[g] |
| *Acinetobacter* | 33; 196 | — | — | — | — | 298 | — | — | 74 | — | 8 | 48 | 40 | 1[h] |
| *Aeromonas* | — | — | — | — | 52 | — | — | — | — | 99 | 4 | 67 | 66 | 1[j] |
| *Corynebacterium/ Rhodococcus* | — | — | — | 105 | — | — | — | — | 40 | — | 45/3 | 104/25 | 100/24 | 2[k] |

TABLE 4-continued

Genus specificity of partial TRF profiles for blood pathogens

| Organisms[a] | Alu I[b] 6FAM | Alu I[b] HEX | Hha I[b] 6FAM | Hha I[b] HEX | Msp I[b] 6FAM | Msp I[b] HEX | Rsa I[b] 6FAM | Rsa I[b] HEX | Hha I[c] 6FAM | Hha I[c] HEX | Species | Genus profiles[d] | Same genus matches | Different genus matches |
|---|---|---|---|---|---|---|---|---|---|---|---|---|---|---|
| Bartonella | — | 346 | — | — | 369 | 300 | — | — | — | — | 7 | 29 | 27 | 0 |
| Campylobacter | — | — | 59 | — | 431 | — | — | — | — | — | 6 | 12 | 12 | 0 |
| Enterobacteriaceae: Citrobacter, Enterobacter, Erwinia, Escherichia, Hafnia, Klebsiella, Kluyvera, Proteus, Rahnella, Salmonella, Serratia, and Shigella | 35 | — | 333 | — | — | 81 | — | — | — | — | — | 170 | 180 | 3[m] |

[a]Organisms are presented in approximate order of incidence for isolation from blood culture at Marshfield Laboratories.
[b]Labeled fragments derived from the PCR product of (6FAM)-S-D-Bact-0045-b-S-20 and (HEX)-S-D-Bact-0785-a-A-19.
[c]Labeled fragments derived from the PCR product of (6FAM)-S-D-Bact-0785-a-S-19 and (HEX)-S-D-Bact-1371-a-A-20.
[d]Total number of profiles of a given genus in the TRFPD (as of Jan. 1, 2003) compiled from experimental and sequence predicted data.
[e]The non-enterococcal match is for one *Aeromonas* profile out of 67 in the TRFPD.
[f]The non-streptococcal match is for one *Shewanella* out of 46 in the TRFPD.
[g]The non-bacteroidal matches are for *Porphyromonas* (2/12) and *Prevotella* (1/27).
[h]The non-acinetobacterial match is for one *Alcaligenes* out of 24 in the TRFPD.
[j]The non-aeromonal match is for one *Haemophilus* out of 57 in the TRFPD.
[k]The non-corynebacterial/rhodococcal matches are for *Brevibacterium* (1/10) and *Tropheryma* (1/1).
[m]The non-enteric matches are for *Pseudomonas* (1/177), *Rhodococcus* (3/25), and *Yersinia* (5/27).

Detection of nuc and mecA:

The presence of nuc was confirmed in all tested strains of *S. aureus* (ATCC 25923, ATCC 29213, ATCC 43300, MC 53R, MC 91, MC 97R, MC 98R, MC 99R, and MC 100R).

Figures 4, 4A, 4B, 4C:
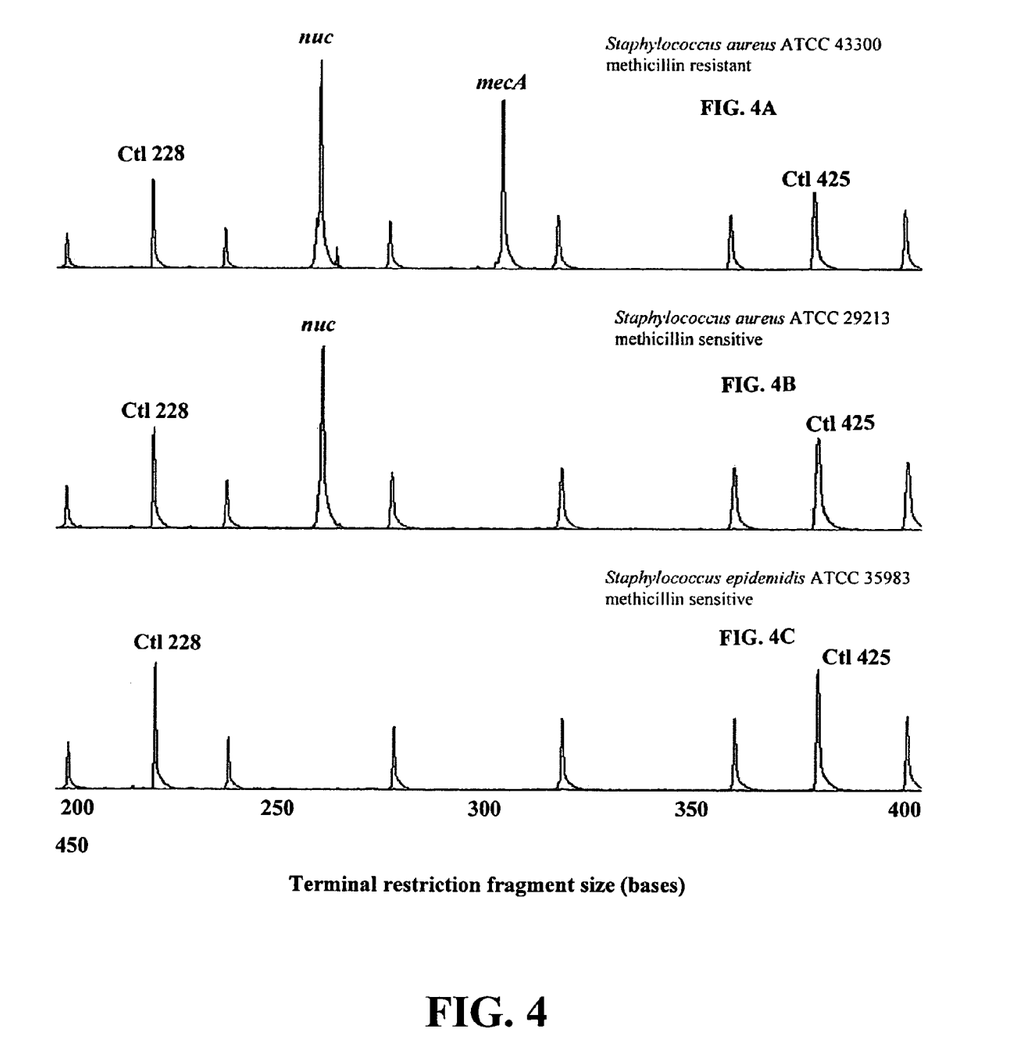
FIG. 4 is a series of representative composite electropherograms of TRF profiles for detection of nuc and mecA from staphylococci.
FIG. 4A shows *Staphylococcus aureus* ATCC 43300.
FIG. 4B shows *Staphylococcus aureus* ATCC 29213.
FIG. 4C shows *Staphylococcus epidemidis* ATCC 35983.

As illustrated in FIG. 4A–4C, a 279 base TAMRA-labeled TRF from the Hha I digested product of a triplex PCR, derived from the primers TAMRA-nuc-S and nuc-A, was detected only in *S. aureus* strains. Each panel includes the TAMRA-labeled PCR product/restriction digest for each representative staphylococcal strain and the applicable range of the ROX standard curve. FIG. 4A shows *S. aureus* ATCC 43300, methicillin resistant, with the presence of nuc (279 bases) and mecA (331–334 bases) screened from the Hha I digest of PCR products from the primers TAMRA-nuc-S and TAMRA-mecA-S, respectively. FIG. 4B shows *S. aureus* ATCC 29213, methicillin sensitive, with the TAMRA labeled Hha I restriction digest/fragment size controls indicated as Ctl 228 and Ctl 425. The other staphylococci (*S. epidermidis* ATCC 35983 (FIG. 4C), *S. saprophyticus* MC 28R, and *S. haemolyticus* ATCC 29970) did not have a TAMRA-labeled TRF above background level in the 279±3 base window, indicating the absence of nuc in these strains.

Several *S. aureus* strains with previously determined methicillin phenotypes were screened for the presence of mecA by TRF sizing. A 331 or 334 base TAMRA-labeled TRF from the Hha I digested product of a triplex PCR, derived from the primers TAMRA-mecA-S and mecA-A, was detected only in *S. aureus* strains determined to be methicillin resistant (ATCC 43300, MC 53R, MC 97R, and MC 98R) (see representative electropherograms in FIG. 4). The methicillin sensitive strains of *S. aureus* (ATCC 25923, ATCC 29213, MC 91, MC 99R, and MC 100R) and other staphylococci (*S. epidermidis* ATCC 35983, *S. saprophyticus* MC 28R, and *S. haemolyticus* ATCC 29970) did not have a TAMRA-labeled TRF above background level in the 333±3 base window, suggesting the absence of mecA in these strains.

The present invention allows for the differentiation of a wide variety of bacteria known to be isolated from blood culture. TRF profiles represent sequence predicted information, thereby offering an advantage over single-stranded conformation polymorphism (SSCP) analysis, as additional primer sets can be more easily incorporated into the identification scheme. TRF profiling for bacterial identification is more rapid than sequencing of the 16S rRNA gene, primarily because it does not require a second thermal cycler reaction to produce sequencable terminated products.

It is understood that the invention is not confined to the particular construction and arrangement of parts herein illustrated and described, but embraces such modified forms thereof as come within the scope of the claims following the Bibliography.

BIBLIOGRAPHY

1. Amann, R. I., W. Ludwig, and K. H. Schleifer. 1995. Phylogenetic identification and in situ detection of individual microbial cells without cultivation. Microbiol. Rev. 59:143–169.
2. Avaniss-Aghajani, E., K. Jones, A. Holtzman, T. Aronson, N. Glover, M. Boian, S. Froman, and C. F. Brunk. 1996. Molecular technique for rapid identification of Mycobacteria. J. Clin. Microbiol. 34:98–102.
3. Brakstad, O. G., K. Aasbakk, and J. A. Maeland. 1992. Detection of *Staphylococcus aureus* by polymerase chain reaction amplification of the nuc gene. J. Clin. Microbiol. 30:1654–1660.

4. Browne, K., J. Miegel, and K. D. Stottmeier. 1984. Detection of pneumococci in blood cultures by latex agglutination. J. Clin. Microbiol. 19:649–650.

5. Brunk, C. F., E. Avaniss-Aghajani, and C. A. Brunk. 1996. A computer analysis of primer and probe hybridization potential with bacterial small-subunit rRNA sequences. Appl. Environ. Microbiol. 62:872–879.

6. Chen, K., H. Neimark, P. Rumore, and C. R. Steinman. 1989. Broad range DNA probes for detecting and amplifying eubacterial nucleic acids. FEMS Microbiol. Lett. 48:19–24.

7. Chen, Y. C., J. D. Eisner, M. M. Kattar, S. L. Rassoulian-Barrett, K. Lafe, U. Bui, A. P. Limaye, and B. T. Cookson. 2001. Polymorphic internal transcribed spacer region 1 DNA sequences identify medically important yeasts. J. Clin. Microbiol. 39:4042–4051.

8. Denis, F., J. Fleurette, G. Laurans, A. Moulin, M. Mounier, J. Orfila, and M. E. Reverdy. 1984. A latex agglutination technique for rapid, direct identification of pneumococci in blood cultures. Eur. J. Clin. Microbiol. 3:321–322.

9. Doern, G. V., R. Vautour, M. Gaudet, and B. Levy. 1994. Clinical impact of rapid in vitro susceptibility testing and bacterial identification. J. Clin. Microbiol. 32:1757–1762.

10. Fredricks, D. N., and D. A. Relman. 1999. Application of polymerase chain reaction to the diagnosis of infectious diseases. Clin. Infect. Dis. 29:475–486.

11. Fredricks, D. N., and D. A. Relman. 1998. Improved amplification of microbial DNA from blood cultures by removal of the PCR inhibitor sodium polyanetholesulfonate. J. Clin. Microbiol. 36:2810–2816.

12. Gordon, L. P., M. A. Damm, and J. D. Anderson. 1987. Rapid presumptive identification of streptococci directly from blood cultures by serologic tests and the L-pyrrolidonyl-beta-naphthylamide reaction. J. Clin. Microbiol. 25:238–241.

13. Grisold, A. J., E. Leitner, G. Muhlbauer, E. Marth, and H. H. Kessler. 2002. Detection of methicillin-resistant Staphylococcus aureus and simultaneous confirmation by automated nucleic acid extraction and real-time PCR. J. Clin. Microbiol. 40:2392–2397.

14. Jarvis, W. R. 1996. Selected aspects of the socioeconomic impact of nosocomial infections: morbidity, mortality, cost, and prevention. Infect. Control Hosp. Epidemiol. 17:552–557.

15. Kitts, C. L. 2001. Terminal restriction fragment patterns: a tool for comparing microbial communities and assessing community dynamics. Curr. Issues Intest. Microbiol. 2:17–25.

16. Lem, P., J. Spiegelman, B. Toye, and K. Ramotar. 2001. Direct detection of mecA, nuc and 16S rRNA genes in BacT/Alert blood culture bottles. Diagn. Microbiol. Infect. Dis. 41:165–168.

17. Louie, L., J. Goodfellow, P. Mathieu, A. Glatt, M. Louie, and A. E. Simor. 2002. Rapid detection of methicillin-resistant staphylococci from blood culture bottles by using a multiplex PCR assay. J. Clin. Microbiol. 40:2786–2790.

18. Maes, N., J. Magdalena, S. Rottiers, Y. De Gheldre, and M. J. Struelens. 2002. Evaluation of a triplex PCR assay to discriminate Staphylococcus aureus from coagulase-negative Staphylococci and determine methicillin resistance from blood cultures. J. Clin. Microbiol. 40:1514–1517.

19. Maidak, B. L., J. R. Cole, T. G. Lilburn, C. T. Parker, Jr., P. R. Saxman, R. J. Farris, G. M. Garrity, G. J. Olsen, T. M. Schmidt, and J. M. Tiedje. 2001. The RDP-II (Ribosomal Database Project). Nucleic Acids Res. 29:173–174.

20. Maquelin, K., C. Kirschner, L. P. Choo-Smith, N. A. Ngo-Thi, T. van Vreeswijk, M. Stammler, H. P. Endtz, H. A. Bruining, D. Naumann, and G. J. Puppels. 2003. Prospective study of the performance of vibrational spectroscopies for rapid identification of bacterial and fungal pathogens recovered from blood cultures. J. Clin. Microbiol. 41:324–329.

21. Marsh, T. L. 1999. Terminal restriction fragment length polymorphism (T-RFLP): an emerging method for characterizing diversity among homologous populations of amplification products. Curr. Opin. Microbiol. 2:323–327.

22. Marsh, T. L., P. Saxman, J. Cole, and J. Tiedje. 2000. Terminal restriction fragment length polymorphism analysis program, a web-based research tool for microbial community analysis. Appl. Environ. Microbiol. 66:3616–3620.

23. Murakami, K., W. Minamide, K. Wada, E. Nakamura, H. Teraoka, and S. Watanabe. 1991. Identification of methicillin-resistant strains of staphylococci by polymerase chain reaction. J. Clin. Microbiol. 29:2240–2244.

24. Oliveira, K., S. M. Brecher, A. Durbin, D. S. Shapiro, D. R. Schwartz, P. C. De Girolami, J. Dakos, G. W. Procop, D. Wilson, C. S. Hanna, G. Haase, H. Peltroche-Llacsahuanga, K. C. Chapin, M. C. Musgnug, M. H. Levi, C. Shoemaker, and H. Stender. 2003. Direct identification of Staphylococcus aureus from positive blood culture bottles. J. Clin. Microbiol. 41:889–891.

25. Qian, Q., Y. W. Tang, C. P. Kolbert, C. A. Torgerson, J. G. Hughes, E. A. Vetter, W. S. Harmsen, S. O. Montgomery, F. R. Cockerill, 3rd, and D. H. Persing. 2001. Direct identification of bacteria from positive blood cultures by amplification and sequencing of the 16S rRNA gene: evaluation of BACTEC 9240 instrument true-positive and false-positive results. J. Clin. Microbiol. 39:3578–3582.

26. Ratner, H. B., and C. W. Stratton. 1985. Thermonuclease test for same-day identification of Staphylococcus aureus in blood cultures. J. Clin. Microbiol. 21:995–996.

27. Relman, D. A., J. S. Loutit, T. M. Schmidt, S. Falkow, and L. S. Tompkins. 1990. The agent of bacillary angiomatosis. An approach to the identification of uncultured pathogens. N. Engl. J. Med. 323:1573–1580.

28. Ruoff, K. L., R. A. Whiley, and D. Beighton. 1999. Streptococcus, p. 283–296. In P. R. Murray, E. J. Baron, M. A. Pfaller, F. C. Tenover, and R. H. Yolken (ed.), Manual of Clinical Microbiology, 7th ed. ASM press, Washington, D.C.

29. Shin, J. H., F. S. Nolte, B. P. Holloway, and C. J. Morrison. 1999. Rapid identification of up to three Candida species in a single reaction tube by a 5' exonuclease assay using fluorescent DNA probes. J. Clin. Microbiol. 37:165–170.

30. Shin, J. H., F. S. Nolte, and C. J. Morrison. 1997. Rapid identification of Candida species in blood cultures by a clinically useful PCR method. J. Clin. Microbiol. 35:1454–1459.

31. Southern, E. M. 1979. Measurement of DNA length by gel electrophoresis. Anal. Biochem. 100:319–323.

32. Turenne, C. Y., E. Witwicki, D. J. Hoban, J. A. Karlowsky, and A. M. Kabani. 2000. Rapid identification of bacteria from positive blood cultures by fluorescence-based PCR-single-strand conformation polymorphism analysis of the 16S rRNA gene. J. Clin. Microbiol. 38:513–520.
33. Wellstood, S. A. 1987. Rapid, cost-effective identification of group A streptococci and enterococci by pyrrolidonyl-beta-naphthylamide hydrolysis. J. Clin. Microbiol. 25:1805–1806.
34. Widjojoatmodjo, M. N., A. C. Fluit, and J. Verhoef. 1995. Molecular identification of bacteria by fluorescence-based PCR-single-strand conformation polymorphism analysis of the 16S rRNA gene. J. Clin. Microbiol. 33:2601–2606.
35. Woese, C. R. 1987. Bacterial evolution. Microbiol. Rev. 51:221–271.

What is claimed is:

1. A method of identifying bacteria in a biological sample, the method comprising:

(a) isolating nucleic acid present within a known species of bacteria;

(b) specifically amplifying the isolated nucleic acid from step (a) by the polymerase chain reaction using at least two distinct, non-overlapping pairs of labeled primers, wherein the primers selectively prime amplification of DNA encoding bacterial 16S rRNA from the known species of bacteria, thereby yielding bacteria-specific amplicons for the known species of bacteria; wherein the bacteria-specific amplicons do not overlap in sequence (c) digesting the amplicons of step (b) with at least one restriction endonuclease to yield restriction fragments;

(d) size-sorting the restriction fragments from step (c) to yield a restriction fragment length profile for the known species of bacteria; and (e) repeating steps (a) through (d) for other known species of bacteria, to yield a database of standard restriction fragment length profiles for each known species of bacteria; and (f) isolating nucleic acid present within the biological sample and repeating steps (b) through (d) to yield a restriction fragment length profile for the biological sample; and then (g) comparing the restriction fragment length profile for the biological sample of step (f) to the database of step (e), whereby bacteria present in the biological sample are identified, at the species level.

2. The method of claim 1, wherein the biological sample is a blood sample.

3. The method of claim 1 wherein the identification can be completed within 8 hours.

4. The method of claim 1, wherein the identification can be completed without subculturing the biological sample.

5. The method of claim 1, wherein the primers in step (b) are labeled with differentially detectable fluorophores.

6. A method of identifying bacteria in a biological sample, the method comprising:
   (a) isolating nucleic acid present within the biological sample;
   (b) specifically amplifying the isolated nucleic acid from step (a) by the polymerase chain reaction using at least two distinct, non-overlapping pairs of labeled primers selected from the group consisting of SEQ. ID. Nos. 1–4, wherein the primers selectively prime amplification of DNA encoding bacterial 16S rRNA, thereby yielding bacteria-specific amplicons; wherein the bacteria-specific amplicons do not overlap in sequence
   (c) digesting the amplicons of step (b) with at least one restriction endonuclease to yield restriction fragments;
   (d) size-sorting the restriction fragments from step (c) to yield a restriction fragment length profile for the biological sample; and
   (e) repeating steps (a) through (d) for known species of bacteria, to yield a database of standard restriction fragment length profiles; and then
   (f) comparing the restriction fragment length profile for the biological sample to the database of step (e), whereby bacteria present in the biological sample are identified, at the species level.

7. The method of claim 1, wherein the amplicons of step (c) are digested using an enzyme selected from the group consisting of Alu I, Hha I, Msp I, Rsa I, Aat II, AccI, AccI11, Acc65 I, AccB7 I, Acy I, Age 1, Alu 1, Alw26 I, Alw44I, Apa 1, Ava I, Ava 1I, BalI, BamH 1, Ban I, Ban II, Bbu 1, Bcl I, Bgl 1, Bgl II, BsaM I, BsaO I, Bsp1286 I, BsrBR I, BsrS I, BssH II, Bst71 I, Bst98 I, BstE II, BstO I, BstX I, BstZ I, Bsu36 I, Cfo I, Cla 1, Csp I, Csp 45 I, Dde I, Dpn I, Dra 1, EclHK I, Eco47 III, Eco52 I, Eco72 I, EcoI CR I, EcoR I, EcoR II EcoR V, Fok I, Hae II, Hae III, Hha I, Hinc II, Hind III, Hinf I, Hpa I, Hpa II, Hsp92 I, Hsp92 II, I-Ppo I, Kpn I, Mbo I, Mbo II, Mlu I, Msp I, MspA I, Nae I, Nar, Nci I, Nco I, Nde 1. NgoM I, Nhe I, Not I, Nru I, Nsi 1, Pst I, Pvu I, Rvu II, Rsa I, Sac I, Sac II, Sal I, Sau3A I, Sau96 I, Sca I, Sfi I, Sgf I, Sin I, Sma I, SnaB I, Spe I, Sph I, Ssp I, Sst I, Stu I, Sty I, Taq I, Tru9 I, Tth111 I, Vsp I, Xba I, Xho I, Xho II, Xma 1, and Xmn I.

8. A method of identifying bacteria in a biological sample, the method comprising:
   (a) amplifying isolated nucleic acid by the polymerase chain reaction from a plurality of known species or strains of bacteria using at least two distinct, non-overlapping pairs of labeled primers, wherein the primers selectively prime amplification of DNA encoding bacterial 16S rRNA from each known species or strain of bacteria, thereby yielding bacteria-specific amplicons for each known species or strain of bacteria; wherein the bacteria-specific amplicons do not overlap in sequence
   (b) sub-dividing the amplicons of step (b) into sub-samples, and digesting each sub-sample with at least one restriction endonuclease to yield restriction fragments;
   (c) size-sorting the restriction fragments from step (b) to yield a distinct restriction fragment length profile corresponding to each species and strain tested, and each restriction endonuclease employed, and compiling the profiles into a searchable database;
   (d) isolating nucleic acid present within the biological sample;
   (e) specifically amplifying the isolated nucleic acid from step (d) via the polymerase chain reaction using the same primers utilized in step (a), thereby yielding bacteria-specific amplicons;
   (f) digesting the amplicons of step (e) with at least one restriction endonuclease used in step (b) to yield restriction fragments;
   (g) size-sorting the restriction fragments from step (f) to yield a restriction fragment length profile for the biological sample; and
   (h) comparing the restriction fragment length profile for the biological sample to the database of step (c), whereby bacteria present in the biological sample are identified at the species level.

9. The method of claim 8, wherein the biological sample is a blood sample.

10. The method of claim 8, wherein the identification can be completed within 8 hours.

11. The method of claim 8, wherein the identification can be completed without subculturing the biological sample.

12. The method of claim 8, wherein the primers are labeled with differentially detectable fluorophores.

13. A method of identifying bacteria in a biological sample, the method comprising:
   (a) amplifying isolated nucleic acid via the polymerase chain reaction from a plurality of known genera, species, or strains of bacteria using at least two distinct, non-overlapping pairs of labeled primers selected from the group consisting of SEQ. ID. Nos. 1–4, wherein the primers selectively prime amplification of DNA encoding bacterial 16S rRNA, thereby yielding bacteria-specific amplicons; wherein the bacteria-specific amplicons do not overlap in sequence
   (b) sub-dividing the amplicons of step (b) into sub-samples, and digesting each sub-sample with at least one restriction endonuclease to yield restriction fragments;
   (c) size-sorting the restriction fragments from step (b) to yield a distinct restriction fragment length profile corresponding to each genus, species, and strain tested, and each restriction endonuclease employed, and compiling the profiles into a searchable database;
   (d) isolating nucleic acid present within the biological sample;
   (e) specifically amplifying the isolated nucleic acid from step (d) via the polymerase chain reaction using the same primers utilized in step (a), thereby yielding bacteria-specific amplicons;
   (f) digesting the amplicons of step (e) with at least one restriction endonuclease used in step (b) to yield restriction fragments;
   (g) size-sorting the restriction fragments from step (f) to yield a restriction fragment length profile for the biological sample; and
   (h) comparing the restriction fragment length profile for the biological sample to the database of step (c), whereby bacteria present in the biological sample are identified at the species level.

14. The method of claim 8, wherein the amplicons of step (b) are digested using an enzyme selected from the group consisting of Alu I, Hha I, Msp I, Rsa I, Aat II, AccI, AccI11, Acc65 I, AccB7 I, Acy I, Age 1, Alu 1, Alw26 I, Alw44I, Apa 1, Ava I, Ava 1I, BalI, BamH 1, Ban I, Ban II, Bbu 1, Bcl I, Bgl 1, Bgl II, BsaM I, BsaO I, Bsp1286 I, BsrBR I, BsrS I, BssH II, Bst71 I, Bst98 I, BstE II, BstO I, BstX I, BstZ I, Bsu36 I, Cfo I, Cla 1, Csp I, Csp 45 I, Dde I, Dpn I, Dra 1, EclHK I, Eco47 III, Eco52 I, Eco72 I, EcoI CR I, EcoR I, EcoR II EcoR V, Fok I, Hae II, Hae III, Hha I, Hinc II, Hind III, Hinf I, Hpa I, Hpa II, Hsp92 I, Hsp92 II, I-Ppo I, Kpn I, Mbo I, Mbo II, Mlu I, Msp I, MspA I, Nae I, Nar, Nci I, Nco I, Nde 1. NgoM I, Nhe I, Not I, Nru I, Nsi 1, Pst I, Pvu I, Rvu II, Rsa I, Sac I, Sac II, Sal I, Sau3A I, Sau96 I, Sca I, Sfi I, Sgf I, Sin I, Sma I, SnaB I, Spe I, Sph I, Ssp I, Sst I, Stu I, Sty I, Taq I, Tru9 I, Tth111 I, Vsp I, Xba I, Xho I, Xho II, Xma 1, and Xmn I.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: S-D-BACT-0045-B-S-20

<400> SEQUENCE: 1
gcytaacaca tgcaagtyga                                                  20

<210> SEQ ID NO 2
<211> LENGTH: 19
<212> TYPE: DNA
<213> ORGANISM: ARTIFICIAL SEQUENCE
<220> FEATURE:
<223> OTHER INFORMATION: S-D-Bact-0045-b-S-20

<400> SEQUENCE: 2
ctaccagggt atctaatcc                                                   19

<210> SEQ ID NO 3
<211> LENGTH: 19
<212> TYPE: DNA
<213> ORGANISM: ARTIFICIAL SEQUENCE
<220> FEATURE:
<223> OTHER INFORMATION: S-D-Bact-0785-a-S-19

<400> SEQUENCE: 3
ggattagata ccctggtag                                                   19

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: S-D-Bact-1371-a-A-20

<400> SEQUENCE: 4
aggcccggga acgtattcac                                                  20

<210> SEQ ID NO 5
<211> LENGTH: 26
<212> TYPE: DNA
<213> ORGANISM: ARTIFICIAL SEQUENCE
<220> FEATURE:
<223> OTHER INFORMATION: TAMRA-nuc-S

<400> SEQUENCE: 5
tamragcgat tgatggtgat acggtt                                           26

<210> SEQ ID NO 6
<211> LENGTH: 24
<212> TYPE: DNA
<213> ORGANISM: ARTIFICIAL SEQUENCE
```

-continued

```
<220> FEATURE:
<223> OTHER INFORMATION: TAMRA-nuc-A

<400> SEQUENCE: 6
agccaagcct tgacgaacta aagc                                          24

<210> SEQ ID NO 7
<211> LENGTH: 27
<212> TYPE: DNA
<213> ORGANISM: ARTIFICIAL SEQUENCE
<220> FEATURE:
<223> OTHER INFORMATION: TAMRA-mecA-S

<400> SEQUENCE: 7
tamraaaaat cgatggtaaa ggttggc                                       27

<210> SEQ ID NO 8
<211> LENGTH: 22
<212> TYPE: DNA
<213> ORGANISM: ARTIFICIAL SEQUENCE
<220> FEATURE:
<223> OTHER INFORMATION: TAMRA-mecA-A

<400> SEQUENCE: 8
agttctgcag taccggattt gc                                            22

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: TAMRA labeled S-D-Bact-0785-a-A-19

<400> SEQUENCE: 9
tamractacc agggtatcta atcc                                          24

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: unlabeled S-D-Bact-0045-b-S-20

<400> SEQUENCE: 10
cgytaacaca tgcaagtyga                                               20
```